(12) United States Patent
Korpel et al.

(10) Patent No.: US 7,824,538 B2
(45) Date of Patent: Nov. 2, 2010

(54) PROCESS FOR IMPROVING THE PURITY OF QUATERNARY AMMONIUM HYDROXIDES BY ELECTROLYSIS IN A TWO-COMPARTMENT CELL

(75) Inventors: Fred Korpel, Roosendaal (NL); Gerrit Jan Boerman, Deventer (NL); Roger Keranen Rains, Richfield, OH (US)

(73) Assignee: Flexsys B.V., Deventer (NL)

( * ) Notice: Subject to any disclaimer, the term of this patent is extended or adjusted under 35 U.S.C. 154(b) by 1204 days.

(21) Appl. No.: 10/489,161

(22) PCT Filed: Oct. 7, 2002

(86) PCT No.: PCT/EP02/11454

§ 371 (c)(1),
(2), (4) Date: May 7, 2004

(87) PCT Pub. No.: WO03/033121

PCT Pub. Date: Apr. 24, 2003

(65) Prior Publication Data
US 2005/0006252 A1 Jan. 13, 2005

(30) Foreign Application Priority Data
Oct. 12, 2001 (EP) .................... 01203863

(51) Int. Cl.
*C02F 9/06* (2006.01)
(52) U.S. Cl. ............... 205/746; 205/431; 205/686; 205/703
(58) Field of Classification Search ............. 205/431, 205/688, 746, 703; 510/253
See application file for complete search history.

(56) References Cited

U.S. PATENT DOCUMENTS

| | | | |
|---|---|---|---|
| 3,250,691 A * | 5/1966 | Broun, Jr. et al. ......... 205/342 |
| 3,844,911 A * | 10/1974 | Ruehlen ............... 205/417 |
| 3,992,301 A | 11/1976 | Shippey et al. |
| 4,144,185 A | 3/1979 | Block |
| 4,394,226 A | 7/1983 | Wade et al. |
| 4,402,804 A * | 9/1983 | Jackson ............... 205/452 |
| 4,572,769 A | 2/1986 | Shimizu |
| 4,714,530 A | 12/1987 | Hale et al. |
| 4,715,939 A | 12/1987 | Ball et al. .......... 204/182.4 |
| 5,288,384 A * | 2/1994 | Banerjee ............. 204/252 |
| 5,389,211 A | 2/1995 | Sharifian et al. |
| 5,623,088 A * | 4/1997 | Stern et al. ............ 564/112 |
| 6,140,538 A | 10/2000 | Van Hengstum et al. |
| 2002/0079233 A1 * | 6/2002 | Giatti et al. ........... 205/431 |

FOREIGN PATENT DOCUMENTS

WO  WO 02 34372 A    5/2002
WO  WO 02/34372 A3   5/2002

* cited by examiner

*Primary Examiner*—Mark F Huff
*Assistant Examiner*—Rashid Alam
(74) *Attorney, Agent, or Firm*—Brinks Hofer Gilson & Lione

(57) ABSTRACT

The present invention relates to a process for purifying a recycle base solution waste stream of a composition comprising a quaternary ammonium hydroxide comprising the steps of (a) providing an electrolysis cell which comprises an anolyte compartment containing an anode, a catholyte compartment containing a cathode, and a cation-selective membrane separating the anolyte and catholyte compartments, (b) charging the recycle base solution waste stream comprising the quaternary ammonium hydroxide to be purified to the anolyte compartment and charging water, optionally containing a quaternary ammonium hydroxide, to the catholyte compartment, (c) passing a current through the electrolysis cell to produce a purified aqueous quaternary ammonium hydroxide solution in the catholyte compartment, (d) recovering the purified aqueous quaternary ammonium hydroxide solution from the catholyte compartment, (e) washing the anolyte compartment with a suitable solvent, and (f) repeating steps (b)-(e). The process is particularly suitable for improving the purity of an aqueous solution comprising tetramethyl ammonium hydroxide, which was used in the production of 4-aminodiphenylamine for a number of reaction cycles.

11 Claims, No Drawings

PROCESS FOR IMPROVING THE PURITY OF QUATERNARY AMMONIUM HYDROXIDES BY ELECTROLYSIS IN A TWO-COMPARTMENT CELL

The present invention relates to a process for improving the purity of a recycle base solution waste stream comprising a quaternary ammonium hydroxide.

Quaternary ammonium hydroxides such as tetramethyl ammonium hydroxide (TMAH) are used inter alia as a developer for photoresists in the manufacture of printed circuit boards and microelectronic chips and as a base in the production of 4-aminodiphenylamine (4-ADPA). Alkylated derivatives of 4-ADPA such as N-(1,3-dimethylbutyl)-N'-phenyl-p-phenylenediamine (6-PPD) are used as antidegradants in rubber compositions and rubber articles such as tires.

In said production of 4-ADPA, the base—which typically is in the form of an aqueous solution—is recycled many times (hereinafter also referred to as recycle base solution). However, after a certain number of reaction cycles, the active content of the aqueous base solution has decreased to such an extent that it can no longer be used in the production process and either some of the recycle aqueous base solution is purged and replaced with fresh waste solution or all of it is discarded as waste, which adds to the cost of the 4-ADPA and the 6-PPD prepared thereof. The present invention provides a solution to this waste problem. Also, with an increasing number of reaction cycles, the liquid-liquid separation of the aqueous waste solution from the 4-ADPA-containing organic phase proceeds with greater difficulty.

When TMAH is used as the base, the purged/discarded aqueous recycle base solution contains inter alia various tetramethyl ammonium (TMA) salts, such as tetramethyl ammonium acetate, formate, chloride, carbonate, and oxalate as well as aniline—one of the starting materials for preparing 4-ADPA. It further contains small amounts of various other salts and other organic impurities. Quaternary ammonium hydroxides are typically prepared by means of electrolysis. For example, TMAH may be prepared from tetramethyl ammonium chloride using a two-compartment electrolysis cell comprising an anolyte compartment containing an anode and a catholyte compartment containing a cathode, said compartments being separated by a cation-selective membrane. Said membrane is also referred to in the art as a cation-exchange membrane. In this manufacturing process, the quaternary ammonium salt from which the quaternary ammonium hydroxide is prepared is charged to the anolyte compartment. A method of manufacturing TMAH was disclosed in U.S. Pat. No. 4,572,769. This method describes the synthesis of TMAH from tetramethyl ammonium formate by electrolysis, however, not the purification of TMAH from a recycle base solution. In U.S. Pat. No. 4,394,226 similarly, TMAH is prepared from tetramethyl ammonium halide, particularly chloride, in an electrolytic cell, but no purification of a recycle base solution containing TMAH was disclosed.

It is also known in the art to improve the purity of mixtures comprising a quaternary ammonium hydroxide by electrolysis.

For example, U.S. Pat. No. 4,714,530 discloses a process for producing high-purity quaternary ammonium hydroxides by means of electrolysis using a two-compartment electrolysis cell equipped with a cation-exchange membrane in which an aqueous solution containing the quaternary ammonium hydroxide is charged to the anolyte compartment. This method does not relate to a recycle base solution containing TMAH, but relates to improving the purity of freshly prepared TMAH, which process, moreover, makes use of a method leading to deposition of solid material at the anode.

We found that the electrolysis of the waste stream of recycle TMAH—as obtained from the production of 4-ADPA—by charging it to the anolyte compartment of a two-compartment electrolysis cell soon after its start resulted in the formation of a significant amount of a solid material at the anode, which fouled the electrode and the anolyte compartment and virtually stopped the electrolysis after some time (see Comparative Examples A and B).

Surprisingly, we subsequently found that these problems were less severe or even did not occur when the electrolysis was carried out in accordance with the present invention.

The process for purifying a recycle base solution waste stream of a composition comprising a quaternary ammonium hydroxide in accordance with the present invention comprises the steps of (a) providing an electrolysis cell which comprises an anolyte compartment containing an anode, a catholyte compartment containing a cathode, and a cation-selective membrane separating the anolyte and catholyte compartments, (b) charging the recycle base solution waste stream comprising the quaternary ammonium hydroxide to be purified to the anolyte compartment and charging water, optionally containing a quaternary ammonium hydroxide, to the catholyte compartment, (c) passing a current through the electrolysis cell to produce a purified aqueous quaternary ammonium hydroxide solution in the catholyte compartment, (d) recovering the purified aqueous quaternary ammonium hydroxide solution from the catholyte compartment, (e) washing the anolyte compartment with a suitable solvent, and (f) repeating steps (b)-(e).

In the case of recycle base, which is obtained from the production of 4-ADPA, the invention process results in the recovery from the catholyte compartment of an aqueous solution containing lower amounts of anions, such as acetate, formate, chloride, carbonate, and oxalate, than are present in the recycle base and, if desired, having a higher quaternary ammonium hydroxide content. Typically, the recovered aqueous solution also contains a portion/fraction of the neutral organic compounds such as aniline, which are present in the recycle base.

Due to the fact that the anolyte and catholyte compartments contain aqueous solutions, oxygen gas is formed at the anode and hydrogen gas is formed at the cathode. The presence of tetramethyl ammonium carbonate and/or tetramethyl ammonium bicarbonate in the anolyte compartment may cause the formation of carbon dioxide gas, which depends on the pH of the aqueous solution in the anolyte compartment. These gases are handled and processed in a conventional way.

The invention process can be carried out using any known electrolysis cell equipped with conventional electrodes and cation-selective membranes, provided said electrodes and membranes are compatible with the solutions which are charged to and which are formed in the anolyte and catholyte compartments.

The anode and the cathode may be made from a variety of materials. The anode must be suitable for oxygen formation/evolution and the cathode for hydrogen formation/evolution. Suitable anodes and cathodes are known to a person of ordinary skill in the art. The cathode may also be an oxygen reducing/oxygen depolarized cathode. Preferably, a platinum anode and a stainless steel cathode are used.

The cation-selective membrane may be any of those, which have been used in the electrolysis of quaternary ammonium salts to quaternary ammonium hydroxides and the electrolytic purification of quaternary ammonium hydroxides. A variety of suitable cation-selective membranes are available to a person of ordinary skill in the art. A distinction is made between perfluorinated and non-perfluorinated membranes. Preferably, the cation-selective membrane to be used in accordance with the present invention is a perfluorinated membrane, for example made from polytetrafluoroethylene, such as the ones sold under the name Nafion by DuPont. Other suitable cation-selective membranes include membranes made from polyethylene, polypropylene, polyvinylchloride, polystyrene-divinylbenzene, and (sulfonated) polysulfone.

Apart from the fact that cation-selective membranes allow the passage of cations and prevent the transport of anions, said membranes are also selective for the type of cation. For example, in the art proton-selective membranes are known. Preferably, the invention process is carried out using a membrane selective for the quaternary ammonium ion, which is present in the composition comprising the quaternary ammonium hydroxide to be purified.

The quaternary ammonium hydroxide-containing compositions which are purified in accordance with the process of the present invention typically are aqueous solutions containing from 1 to 45, preferably 5 to 40, more preferably 10 to 35 wt. % of quaternary ammonium hydroxide. These compositions may contain an organic solvent. They may also contain an inorganic hydroxide such as sodium hydroxide, potassium hydroxide or cesium hydroxide.

The quaternary ammonium hydroxide-containing composition to be used in the process of the present invention may contain any quaternary ammonium hydroxide. Typically, the composition comprises a tetrahydrocarbyl ammonium hydroxide or hydrocarbylene di(trihydrocarbyl)ammonium dihydroxide. The composition may also comprise a mixture of a quaternary ammonium hydroxide and an inorganic hydroxide. Typical examples include tetramethyl ammonium hydroxide, tetrapropyl ammonium hydroxide, tetrabutyl ammonium hydroxide, choline hydroxide, phenyltrimethyl ammonium hydroxide, benzyltrimethyl ammonium hydroxide, and bis-(dibutylethyl)hexamethylene diammonium hydroxide (hexamethylene 1,6-bis(dibutylethyl)ammonium dihydroxide). Other suitable examples have been described in the prior art cited above, i.e. U.S. Pat. No. 4,714,530 (col. 2, I. 60 through col. 3, I. 2) and U.S. Pat. No. 5,389,211 (col. 5, II. 43-60). Preferably, the composition comprises tetramethyl ammonium hydroxide (TMAH). More preferably, the composition to be purified in accordance with the present invention is an aqueous solution, which was used in the production of 4-ADPA for a number of reaction cycles (i.e. recycle base waste stream), most preferably, an aqueous solution comprising TMAH. The recycle base waste stream typically contains aniline. The recycle base waste stream may also contain an inorganic hydroxide.

The quaternary ammonium hydroxide-containing composition to be used in the process of the present invention may also be a mixture of a recycle base solution and other compounds, such as a quantity of a suitable fresh quaternary ammonium salt or salt mixture that can be converted to the quaternary ammonium hydroxide by electrolysis concurrently with the electrolysis of salts in the recycle base solution. For example, tetramethyl ammonium carbonate and/or tetramethyl ammonium hydrogen carbonate can be added to an aqueous recycle TMAH stream. Addition of a suitable fresh quaternary ammonium salt or salt mixture to a recycle base solution, for production of fresh quaternary ammonium hydroxide concurrently with recovery of quaternary ammonium hydroxide from salts in the recycle base, can also be conducted with an electrolysis cell, which comprises an anolyte compartment containing an anode, a catholyte compartment containing a cathode, and at least one intermediate compartment, which is separated from the anolyte and catholyte compartments by cation-selective membranes.

At the start of electrolysis, the catholyte compartment contains water, optionally containing a quaternary ammonium hydroxide. Preferably, demineralized or soft water is used in the invention process. The conductivity of the catholyte solution in the catholyte compartment is increased by including a quaternary ammonium hydroxide. The presence of electrolytes in the anolyte and catholyte compartments allows current to flow through the electrolysis cell immediately after the start of the electrolysis. It is to be noted that it is not critical to the invention process which electrolyte-containing aqueous solution is present in the catholyte compartment. The choice will mainly be determined by the desired purity and the desired active content of the aqueous quaternary ammonium hydroxide solution to be recovered from the catholyte compartment. Preferably, the desired active content is in the range of 15 to 25 wt. %, more preferably about 20 wt. %.

Preferably, the catholyte compartment contains an aqueous solution of a quaternary ammonium hydroxide, which is the same as the quaternary ammonium hydroxide present in the composition to be purified. A practical catholyte solution to start with is an aqueous 1 to 35, preferably 5 to 25, more preferably 5 to 20 wt. % solution of the quaternary ammonium hydroxide. Preferably, the catholyte compartment is charged with an aqueous quaternary ammonium hydroxide solution of high purity, e.g., a solution having the desired purity. The active content may vary as desired. More preferably, an aqueous TMAH solution is used as the starting catholyte solution.

The invention process is operated either as a batch process or as a semi-continuous process. It is practical to use a batch process. Preferably, the invention process is carried out by charging a batch of the composition comprising the quaternary ammonium hydroxide to be purified to the anolyte compartment and continuing the electrolysis until practically all of the quaternary ammonium ions are removed therefrom before charging a subsequent batch to the anolyte compartment. In the case of recycle base, it was found to be advantageous to dilute the recycle base with water before charging it to the anolyte compartment of the electrolysis cell. The processed batch—present in the anolyte compartment—may either be discarded wholly or partly and is then replaced by or mixed with the subsequent batch, respectively. In the case of recycle base, preferably a part of the processed batch—i.e. the so-called heel—is mixed with a fresh portion of recycle base. More preferably, about equal weight parts of heel and fresh recycle base are charged to the anolyte compartment.

In accordance with the present invention, the anolyte compartment of the electrolysis cell is washed with a suitable solvent. It was found that solid material was formed in the anolyte compartment during the electrolysis of a first batch of the composition comprising the quaternary ammonium hydroxide to be purified, in particular in the case of recycle base. As a result, fouling of the electrode, the anolyte compartment, and the anolyte compartment fluid circulation equipment, i.e. the circulation loop, loop filter, circulation vessel, and circulation pump, occurred. Suitable solvents are those, which dissolve the solid material that is formed without affecting any part of the electrolysis equipment. This can easily be determined by a person of ordinary skill in the art.

Suitable solvents include aniline and N,N-dimethylformamide, N-methyl-2-pyrrolidone, and dimethyl sulfoxide. In the case of recycle base, preferably aniline is used as the solvent. The washing step is carried out at the end of the processing of each batch (or semi-continuously processed batch) using as much of the solvent as necessary. The amount of solvent to be used can easily be determined by a person of ordinary skill in the art. Preferably, after washing with a suitable solvent, the anolyte compartment is washed with water before charging a new batch to the anolyte compartment. In the case of recycle base and when using aniline as the solvent, it is best to remove the aniline by washing with water afterwards.

The solvent washing step typically is carried out at an elevated temperature, preferably 40 to 80° C., more preferably 40 to 60° C., most preferably 40 to 50° C. The washing with water typically is carried out at a temperature of 20 to 50° C.

The electrolysis of the composition comprising the quaternary ammonium hydroxide is effected by applying a direct current between the anode and the cathode with a current density of generally up to 4,000 A/m$^2$. A practical range is from 500 to 1,500 A/m$^2$. The current is applied to the electrolysis cell for a period of time sufficient to allow for the transport of preferably all quaternary ammonium ions from the anolyte compartment to the catholyte compartment. An important parameter for monitoring the progress of the invention process is the pH of the aqueous solution in the anolyte compartment.

During the electrolysis of the composition comprising the quaternary ammonium hydroxide to be purified, the pH of the solution of the anolyte compartment decreases due to the generation of protons in the anolyte compartment and the transport of quaternary ammonium ions from the anolyte compartment to the catholyte compartment. Anions such as chloride ions are unable to pass the cation-selective membrane. A weak acid such as acetic acid, however, is able to pass a cation-selective membrane by way of diffusion. Preferably, the electrolysis is stopped once a pH of 1 to 7, more preferably 4 to 7, even more preferably 4 to 6, most preferably about 5 is reached in the anolyte compartment. If only a part of the processed composition—present in the anolyte compartment—is replaced by a subsequent batch, the pH may be maintained between certain chosen values, e.g., between 5 and 7.

Typically, the aqueous solutions present in the compartments of the electrolysis cell are circulated by means of pumping in a conventional way, for example, by using circulation loops, circulation vessels, and pumps for each compartment separately. These circulation loops may be provided with conventional filters.

During the electrolysis, the temperature of the solutions within the compartments typically is maintained at from 10 to 90° C., preferably 40 to 80° C., more preferably 40 to 60° C., most preferably 40 to 50° C.

The present invention is illustrated by the following Examples.

COMPARATIVE EXAMPLES A AND B

Two one-batch experiments were performed using a two-compartment Micro Flow Cell (from ElectroCell) comprising an anolyte compartment containing an anode and a catholyte compartment containing a cathode, said compartments being separated by means of a cation-selective membrane. EPDM gaskets and Teflon frames were used.

In the first experiment, i.e. Comparative Example A, a Nafion 450 membrane (from DuPont) was used. The anode was a platinum electrode, the cathode stainless steel (both from ElectroCell). The recycle base was charged to the anolyte compartment and it contained 13.61 wt. % TMAH. The starting catholyte solution was 13.85 wt. % aqueous TMAH.

In the second experiment, i.e. Comparative Example B, a Nafion 117 membrane was used. The anode was a DSA for oxygen evolution, the cathode stainless steel (both from ElectroCell). The recycle base was charged to the anolyte compartment and it contained 12.68 wt. % TMAH, the catholyte was 12.09 wt. % aqueous TMAH.

The results of these experiments are shown in Tables 1 to 3.

It was found that at the anode a significant amount of a solid material was formed which fouled the electrode and had to be removed periodically in order to be able to continue the electrolysis. Ultimately, the electrolysis virtually stopped (TMA$^+$ bound to carbonate was not transported from the anolyte to the catholyte compartment). As a result, the electrolysis could not be performed long enough for an economically attractive recovery of TMAH to be obtained. In addition, the removal of this solid was time consuming and cumbersome.

The detection limits are as follows: TMA-acetate (0.0023 wt. %), TMA-formate (0.0013 wt. %), TMA-chloride (0.0015 wt. %), TMA$_2$-carbonate (0.0350 wt. %), TMA$_2$-oxalate (0.0027 wt. %), and TMAH (0.0100 wt. %).

TABLE 1

Electrolysis data

| Comparative Example | A | B |
|---|---|---|
| Average current efficiency (%) | 35 | 19 |
| Average current density (A/m$^2$) | 1300 | 2400 |
| Temperature (° C.) | 46 | 47 |
| DC Voltage (V) | 7.7 | 8.2 |

TABLE 2

Starting and recovered waste compositions

| Comp. Ex. A | | $A_{start}$ | $A_{final}$ | $C_{start}$ | $C_{final}$ |
|---|---|---|---|---|---|
| TMA-Acetate | wt. % | 0.74 | 0.66 | nm | nm |
| TMA-Formate | wt. % | 1.09 | 1.02 | nm | nm |
| TMA-Chloride | wt. % | 0.02 | 0.02 | nm | nm |
| TMA$_2$-Carbonate | wt. % | 12.08 | 18.18 | 0.16 | 0.32 |
| TMA$_2$-Oxalate | wt. % | 1.89 | 1.43 | nm | nm |
| TMAH | wt. % | 13.61 | 0.33 | 13.85 | 21.98 |
| Aniline | wt. % | 1.90 | 0.44 | nd | 0.24 |
| Weight | g | 900 | 830 | 750 | 420 |
| Water added | g | 100 | | | |
| Samples taken | g | | 240 | | 240 |

$A_{start}$ is the starting anolyte solution, $A_{final}$ is the final anolyte solution, $C_{start}$ is the starting catholyte solution, and $C_{final}$ is the final catholyte solution, nm means not measurable (below the detection limit), nd means not determined.

TABLE 3

Starting and recovered waste compositions

| Comp. Ex. B | | $A_{start}$ | $A_{final}$ | $C_{start}$ | $C_{final}$ |
|---|---|---|---|---|---|
| TMA-Acetate | wt. % | 0.67 | 1.08 | nm | nm |
| TMA-Formate | wt. % | 1.06 | 1.25 | nm | nm |

TABLE 3-continued

Starting and recovered waste compositions

| Comp. Ex. B | | $A_{start}$ | $A_{final}$ | $C_{start}$ | $C_{final}$ |
|---|---|---|---|---|---|
| TMA-Chloride | wt. % | 0.02 | 0.02 | nm | nm |
| TMA$_2$-Carbonate | wt. % | 13.25 | 24.98 | nm | nm |
| TMA$_2$-Oxalate | wt. % | 1.86 | 1.65 | nm | nm |
| TMAH | wt. % | 12.68 | nm | 12.09 | 23.44 |
| Aniline | wt. % | 1.79 | 0.56 | nd | 0.47 |
| Weight | g | 900 | 570 | 750 | 530 |
| Water added | g | 100 | | | |
| Samples taken | g | | 120 | | 120 |

$A_{start}$ is the starting anolyte solution, $A_{final}$ is the final anolyte solution, $C_{start}$ is the starting catholyte solution, and $C_{final}$ is the final catholyte solution, nm means not measurable (below the detection limit), nd means not determined.

Example 1

A two-compartment Multi Purpose Cell (from ElectroCell) equipped with a DSA anode, a stainless steel cathode, and a Nafion 324 (from Dupont) cation-selective membrane was operated, according to a procedure similar to the procedure described in Comparative Examples A and B (i.e. 12.5 V, 40-50° C., final pH 5), with 6 batches of recycle base for a total (electrolysis) time of 64 h. Each time, the composition to be electrolyzed consisted of a mixture of 1,600 g of fresh recycle base, having a composition similar to the compositions described in Comparative Examples A and B, and 1,600 g of the so-called heel of the previously processed batch of recycle base (i.e. each batch having a total weight of 3,200 g), and 700 g of the heel were discarded. At the end of the processing of each batch, the purified aqueous TMAH solution was recovered from the catholyte compartment and the anolyte compartment including the anolyte fluid circulation loop and circulation vessel were emptied and the circulation vessel was filled with 1,000 g of aniline. The aniline was circulated for 30 min through the anolyte compartment at 50° C. Then, the aniline wash was removed and the wash procedure was repeated with 1,000 g of water, which was circulated for 5 min at 20-50° C., the water being warmed up during circulation. After each washing procedure, the next 3,200 g batch of recycle base plus heel was charged to the anolyte compartment and subjected to electrolysis.

The capacity of the electrolysis cell remained practically unchanged, i.e. it was 40.31 moles TMA$^+$/m$^2$/h for the first batch and 35.73 moles TMA$^+$/m$^2$/h for the sixth batch (TMA$^+$ stands for tetramethyl ammonium ion). Inspection of the electrolysis cell after the processing of the 6 batches did not show any fouling of the anode, the anolyte compartment or the anolyte compartment fluid circulation equipment.

The invention claimed is:

1. A process for purifying a recycle base solution waste stream of a composition comprising a quaternary ammonium hydroxide comprising the steps of
    (a) providing an electrolysis cell which consisting of an anolyte compartment containing an anode, a catholyte compartment containing a cathode, and a cation-selective membrane separating the anolyte and catholyte compartments,
    (b) charging the recycle base solution waste stream comprising an aqueous solution of the quaternary ammonium hydroxide that was used in the production of 4-aminodiphenylamine, to be purified to the anolyte compartment and charging water, optionally containing a quaternary ammonium hydroxide, to the catholyte compartment,
    (c) passing a current through the electrolysis cell to produce a purified aqueous quaternary ammonium hydroxide solution in the catholyte compartment,
    (d) recovering the purified aqueous quaternary ammonium hydroxide solution from the catholyte compartment,
    (e) washing the anolyte compartment with a suitable solvent to dissolve solid materials fouling the anode and the anolyte compartment, the suitable solvent being one selected from the group of aniline, N,N-dimethylformamide, N-methyl-2-pyrrolidone, and dimethyl sulfoxide, and
    (f) repeating steps (b)-(e).

2. The process according to claim 1 wherein the anolyte compartment is charged with an aqueous solution comprising tetramethyl ammonium hydroxide (TMAH).

3. The process according to claim 1 wherein the anolyte compartment is charged with an aqueous solution containing 5 to 40 wt. % of TMAH.

4. The process according to claim 1 wherein the recycle base solution waste stream further comprises aniline.

5. The process according to claim 1 wherein the catholyte compartment is charged with an aqueous solution of a quaternary ammonium hydroxide, which is the same as the quaternary ammonium hydroxide present in the composition to be purified.

6. The process according to claim 5 wherein the catholyte compartment is charged with an aqueous 5 to 25 wt. % TMAH solution.

7. The process according to claim 1 wherein the electrolysis is stopped once a ph of 1 to 7, preferably 4 to 7, is reached in the anolyte compartment.

8. The process according to claim 1 wherein the cation-selective membrane is a perfluorinated membrane.

9. The process according to claim 1 wherein between steps e) and f) the process further comprises the step of washing the anolyte compartment with water.

10. The process according to claim 1 wherein the recycle base solution waste stream comprises a quaternary ammonium hydroxide and a quantity of a quaternary ammonium salt or a mixture of quaternary ammonium salts that can be converted to the quaternary ammonium hydroxide by electrolysis.

11. The process according to claim 10 wherein the recycle base solution waste stream comprises TMAH and at least one of tetramethyl ammonium carbonate and tetramethyl ammonium hydrogen carbonate.

* * * * *